(12) United States Patent
Wong

(10) Patent No.: US 9,433,579 B2
(45) Date of Patent: Sep. 6, 2016

(54) GROWTH FACTOR SENSITIVE VESICLE

(76) Inventor: Albert Wong, Somerville, MA (US)

(*) Notice: Subject to any disclaimer, the term of this patent is extended or adjusted under 35 U.S.C. 154(b) by 1355 days.

(21) Appl. No.: 12/350,961

(22) Filed: Jan. 9, 2009

(65) Prior Publication Data

US 2009/0274751 A1 Nov. 5, 2009

Related U.S. Application Data

(60) Provisional application No. 61/126,255, filed on May 2, 2008.

(51) Int. Cl.
*A61K 9/127* (2006.01)
*C12N 15/88* (2006.01)
*C12Q 1/00* (2006.01)
*A61K 38/00* (2006.01)

(52) U.S. Cl.
CPC .............. *A61K 9/127* (2013.01); *A61K 38/00* (2013.01)

(58) Field of Classification Search
CPC .......................... A61K 9/127; A61K 38/00
USPC .......................................... 424/450; 435/458
See application file for complete search history.

(56) References Cited

U.S. PATENT DOCUMENTS

| 7,208,465 | B2 * | 4/2007 | Heltovics et al. | 512/2 |
| 2003/0095962 | A1 * | 5/2003 | Ueda et al. | 424/130.1 |
| 2005/0214356 | A1 * | 9/2005 | Joyce | 424/450 |

FOREIGN PATENT DOCUMENTS

WO WO 2006/107786 * 10/2006

OTHER PUBLICATIONS

Ge et al. Effect of membrane fluidity on tyrosine kinase activity of reconstituted epidermal growth factor receptor. Biochemical and Biophysical Research Communications 282:511-514, 2001.*
Panayotou et al. reconstitution of the epidermal growth factor receptor in artificial lipid bilayers. FEBS Letters 183:321-325, 1985.*

* cited by examiner

*Primary Examiner* — Quang Nguyen
(74) *Attorney, Agent, or Firm* — Albert Wong

(57) ABSTRACT

A generally spherical growth factor sensitive vesicle bearing growth factor receptors (12) having chemical compounds (14) covalently cross-linked to their non-growth factor binding domains. The chemical compounds are capable of associating to form larger chemical compounds (16) capable of destabilizing the vesicle. Methods for treating growth factor-overexpressing neoplasms are disclosed.

5 Claims, 5 Drawing Sheets

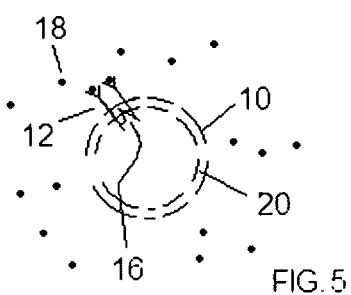

GROWTH FACTOR SENSITIVE VESICLE

CROSS-REFERENCE TO RELATED APPLICATIONS

This application claims the benefit of provisional patent application Ser. No. 61/126,255, filed 2008 May 2, by the present inventor.

FEDERALLY SPONSORED RESEARCH

Not Applicable

SEQUENCE LISTING OR PROGRAM

Not Applicable

BACKGROUND OF THE INVENTION

1. Field of Invention

This invention generally relates to vesicular systems, specifically to a growth factor-sensitive vesicle.

2. Prior Art

Currently, conventional treatments for growth factor-overexpressing neoplasms are generally limited to surgery, radiation therapy, and generalized chemotherapy. Radiation therapy and generalized chemotherapy may result in significant side effects, including an increased risk of new tumor formation. Surgery, when feasible, is attendant with the risk of various surgical complications. Furthermore, combinations of treatments, usually radiation therapy and generalized chemotherapy, and recurring treatments, such as recurring radiation therapy, are often necessary, typically resulting in additional side effects and/or side effects of greater severity.

To achieve the goal of maximizing the effectiveness of chemotherapy while simultaneously minimizing undesirable systemic side effects, the ideal solution would be to use targeted drug delivery to release chemotherapeutic agents specifically in the neighborhood of growth factor-overexpressing neoplasms. Such targeted drug delivery would facilitate chemotherapeutic treatment of the neoplasms by minimizing systemic drug exposure (and hence potentially toxic systemic side effects) while simultaneously maximizing drug exposure to the neoplasms.

A method for such targeted drug delivery that has been researched and used extensively involves the use of vesicles sensitive to artificially generated factors such as ultrasound. However, vesicles sensitive to factors such as ultrasound are typically attendant with the inconvenience and cost associated with the use of external medical equipment, such as an ultrasound machine. Also, it is not always clear, such as in the case of metastatic tumors (where the tumors' precise locations may be unknown), where the factor (for example, ultrasound waves) should be directed.

Since the goal is to treat growth factor-overexpressing neoplasms, the ideal method for targeted drug delivery would involve the use of vesicles sensitive to abnormal (or excessive) amounts of growth factors (that is, growth factor sensitive vesicles). Such growth factor sensitive vesicles would be of great clinical significance because they could be used to specifically release chemotherapeutic agents in the neighborhood of growth factor-overexpressing neoplasms. However, due to the technical challenges inherent in creating a vesicle sensitive to growth factors, no such vesicles have previously been developed. The technical challenges in creating such a vesicle arise because, unlike factors such as ultrasound waves, growth factors do not have the ability to directly destabilize a vesicle.

As such, there is no relevant prior art pertaining to the growth factor sensitive vesicle of the invention.

3. Objects and Advantages

Accordingly, several objects and advantages of the invention are:

(a) to provide a growth factor sensitive vesicle which can carry and deliver a wide variety of chemotherapeutic and other pharmaceutical agents;

(b) to provide a growth factor sensitive vesicle which can be easily manufactured in a wide variety of external and internal dimensions;

(c) to provide a growth factor sensitive vesicle which can have a wide variety of vesicle compositions;

(d) to provide a growth factor sensitive vesicle which can have a wide variety of vesicle surface modifications; and (e) to provide a growth factor sensitive vesicle which can simultaneously be sensitive to other factors, such as ultrasound.

Further objects and advantages will become apparent from a consideration of the ensuing description and drawings.

SUMMARY

In accordance with the present invention a growth factor sensitive vesicle comprises a generally spherical closed body bearing growth factor receptors having chemical compounds covalently cross-linked to their non-growth factor binding domains.

DRAWINGS—FIGURES

A brief description of the invention is hereafter described by non-limiting examples.

FIG. 5 shows a cross-sectional view of a growth factor sensitive vesicle with a destabilized external shell.

DRAWINGS—REFERENCE NUMERALS

10—vesicle
12—growth factor receptor
14—chemical compound
16—larger chemical compound
18—growth factor
20—external shell
22—internal shell

DETAILED DESCRIPTION—FIG. 1—PREFERRED EMBODIMENT

While this invention may be embodied in many different forms, there are described in detail herein specific embodiments of the invention. This description is an exemplification of the principles of the invention and is not intended to limit the invention to the particular embodiments illustrated.

Figure 1:
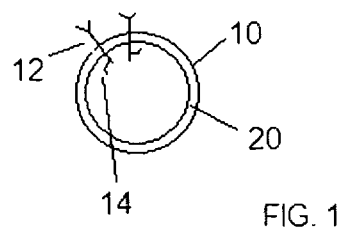
FIG. 1 shows a cross-sectional view of a growth factor sensitive vesicle.

Turning now to the figures, a preferred embodiment of the growth factor sensitive vesicle of the present invention is illustrated in FIG. 1 (cross-sectional view). The vesicle 10 has growth factor receptors 12, covalently cross-linked to chemical compounds 14, incorporated into the external shell 20 of the vesicle 10. Pharmaceutical agents may be bound to the external shell, the growth factor receptors, or the chemical compounds. Pharmaceutical agents may also be incorporated into the external shell, or encapsulated within the external shell. In the preferred embodiment, the external shell is a phospholipid bilayer. However, the external shell can consist of any other material that can form a generally spherical closed body. Also, additional chemical compounds may be cross-linked to the growth factor receptors, and additional growth factor receptors may be incorporated into the external shell.

Figure 4:
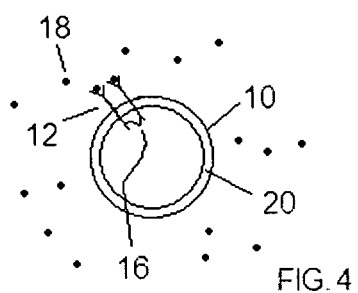
FIG. 4 shows a cross-sectional view of a growth factor sensitive vesicle with growth factors bound to the growth factor receptors.

Operation—FIGS. 4 and 5

A growth factor sensitive vesicle 10, in the preferred embodiment, with growth factors 18 bound to the growth factor receptors 12 is illustrated in FIG. 4 and FIG. 5; in each case a cross-sectional view is shown.

As shown in FIG. 4, when growth factors 18 are bound to the growth factor receptors 12, dimerization of the growth factor receptors 12 occurs, resulting in the chemical compounds 14 (not shown here but shown in FIG. 1) associating to form a larger chemical compound 16 capable of destabilizing the external shell 20 of the vesicle 10. Then, as shown in FIG. 5, the larger chemical compound 16 interacts with and destabilizes the external shell 20 of the vesicle 10, resulting in the release of any pharmaceutical agents carried by the vesicle 10.

Figure 2:
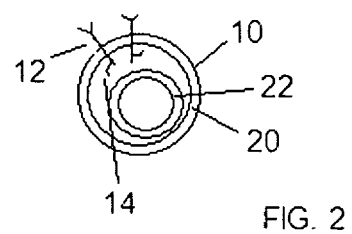
FIG. 2 shows a cross-sectional view of a similar growth factor sensitive vesicle with an internal shell.
Figure 3:
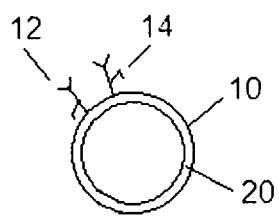
FIG. 3 shows a cross-sectional view of a similar growth factor sensitive vesicle with growth factor receptors bound to the external face of the external shell of the vesicle.

FIGS. 2-3—Additional Embodiments

Additional embodiments are shown in FIG. 2 and FIG. 3; in each case a cross-sectional view is illustrated.

In FIG. 2 the vesicle 10 has an internal shell 22 in addition to an external shell 20 with incorporated growth factor receptors 12 covalently cross-linked to chemical compounds 14. Pharmaceutical agents may be bound to the external shell, the internal shell, the growth factor receptors, or the chemical compounds. Pharmaceutical agents may also be incorporated into the external shell or the internal shell, or encapsulated within the external shell or the internal shell. Additional internal shells may be encapsulated within the external shell. Also, additional chemical compounds may be cross-linked to the growth factor receptors, and additional growth factor receptors may be incorporated into the external shell. Please note that this is only one of a wide variety of possible additional embodiments of the vesicle.

In FIG. 3 the vesicle 10 has growth factor receptors 12, covalently cross-linked to chemical compounds 14, bound to the external face of the external shell 20 of the vesicle. Pharmaceutical agents may be bound to the external shell, the growth factor receptors, or the chemical compounds. Pharmaceutical agents may also be incorporated into the external shell, or encapsulated within the external shell. Additional chemical compounds may be cross-linked to the growth factor receptors. Additional growth factor receptors may be bound to the external shell. Also, additional growth factor receptors may be incorporated into the external shell. Please note that this is only one of a wide variety of possible additional embodiments of the vesicle.

Advantages

From the description above, a number of advantages of the growth factor sensitive vesicle of the invention become evident:

(a) The growth factor sensitive vesicle can be used to carry and deliver a wide variety of pharmaceutical agents specifically in the neighborhood of growth factor-overexpressing neoplasms.
(b) The growth factor sensitive vesicle can be made easily at a wide variety of external and internal dimensions without altering any aspect of its design.
(c) The use of vesicle-borne growth factor receptors to provide vesicle sensitivity to abnormal amounts of growth factors permits a wide variety of vesicle compositions and vesicle surface modifications.
(d) The use of vesicle-borne growth factor receptors to provide vesicle sensitivity to abnormal amounts of growth factors further permits simultaneous vesicle sensitivity to other factors, such as ultrasound, if desired.

Conclusions, Ramifications, and Scope

Accordingly, the reader will see that the growth factor sensitive vesicle of the invention allows all of the benefits associated with the use of a non-growth factor sensitive vesicle while presenting significant additional advantages. It can be used to carry and deliver a wide variety of pharmaceutical agents. It can be easily manufactured with a wide variety of external and internal dimensions, vesicle compositions, and vesicle surface modifications. Most importantly, it can be used to specifically release pharmaceutical agents in the neighborhood of growth factor-overexpressing neoplasms. Furthermore, the growth factor sensitive vesicle of the invention can simultaneously be sensitive to other factors, such as ultrasound.

The above disclosure is intended for illustrative purposes only and is not exhaustive. From the foregoing description, one skilled in the art can readily ascertain the essential characteristics of the invention and, without departing from the spirit and scope thereof, can adapt the invention to various usages and conditions. Changes in the form and substitution of equivalents are contemplated as circumstances may suggest or render expedient, and although specific terms have been employed herein, they are intended in a descriptive sense and not for purposes of limitation. Furthermore, any theories attempting to explain the mechanism of actions have been advanced merely to aid in the understanding of the invention and are not intended as limitations.

Thus the scope of the invention should be determined by the appended claims and their legal equivalents, rather than by the examples given.

What is claimed is:

1. A growth factor sensitive vesicle, comprising:
   an external shell which defines a generally spherical closed body;
   said shell bearing at least two growth factor receptors having functional growth factor binding domains facing outside said shell, at least two of said growth factor receptors each having at least one non-growth factor binding domain covalently cross-linked to at least one chemical compound, at least two of said chemical compounds being capable of associating to form a chemical compound capable of destabilizing or permeabilizing said shell, permitting the release of the contents, if any, orginally enclosed within said shell.

2. The growth factor sensitive vesicle of claim 1, wherein said growth factor sensitive vesicle is selected from a group consisting of a liposome, a niosome, a polyersome, and a vesosome.

3. The growth factor sensitive vesicle of claim 1, wherein said chemical compound capable of destabilizing or permeabilizing said shell is a surface active agent.

4. The growth factor sensitive vesicle of claim 2, wherein said chemical compound capable of destabilizing or permeabilizing said shell is a surface active agent.

5. The growth factor sensitive vesicle of claim 4, wherein said contents originally enclosed within said shell are therapeutically effective for treating a growth factor-overexpressing neoplasm.

* * * * *